Figure 1:
Figure 1:
Figure 1:

United States Patent [19]

Denny et al.

[11] Patent Number: 5,331,004
[45] Date of Patent: Jul. 19, 1994

[54] AROMATIC MUSTARDS AND AZIRIDINES AND PHARMACEUTICAL USES THEREOF

[75] Inventors: William A. Denny, Pakuranga; Graham J. Atwell, Meadowbank, both of New Zealand

[73] Assignee: Circadian Pharmaceuticals (Australia) Pty. Ltd., Toorak, Australia

[21] Appl. No.: 914,783

[22] Filed: Jul. 16, 1992

[51] Int. Cl.⁵ .................. A61K 31/165; C07C 235/56
[52] U.S. Cl. ..................... 514/406; 514/616; 548/364.1; 548/372.5; 548/374.1; 564/86; 564/153; 564/155; 564/156
[58] Field of Search ............... 564/86, 153, 155, 156; 548/378; 514/406, 616

[56] References Cited

FOREIGN PATENT DOCUMENTS

66590/90  6/1991  Australia.
115218    8/1984  European Pat. Off..

OTHER PUBLICATIONS

*Anti-Cancer Drug Design,* vol. 6, No. 3 pp. 195-206, Prakash et al., 1991.
*Dictionary of Organic Compounds, pl Fifth Edition, vol. 3,* published 1982, p. 1613, col. 2, monorraph D-013773.
*Chemical Abstracts,* vol. 99, No. 22, issued Nov. 28, 1983, p. 51, col. 2. Abstract No. 177000v DE 3206138.
*Chemical Abstracts,* vol. 110, No. 9, issued Feb. 27, 1989, p. 599 col. 1, Abstract No. 74991k.

(List continued on next page.)

*Primary Examiner*—Richard L. Raymond
*Attorney, Agent, or Firm*—Price, Heneveld, Cooper, DeWitt & Litton

[57] ABSTRACT

The invention relates to novel polybenzamide mustards having anticancer and hypoxia-selective properties, to methods of preparing the novel compounds, and to the use of these compounds as anticancer agents.

The compounds have general formula (I)

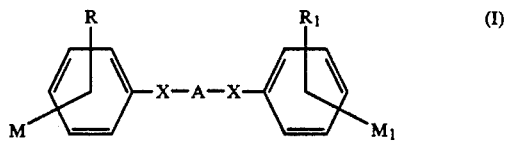

wherein
M and $M_1$ separately represent H, aziridinyl, $N(Et)CH_2CH_2Y$ or $N(CH_2CH_2Y)_2$, where Y is Cl, Br, I or $OSO_2Me$; R and $R_1$ separately represent up to three of H, $NO_2$, aza (ring CH=replaced by N=), $CH_2Q$, $SO_2NHQ$ or CONHQ, where Q is H, Me, $(CH_2)_nNMe_2$ $(CH_2)_nNHC(=NH)NH_2$ and n=2-4);
X represents CONH, NHCO, O, $CH_2$, NH or S; and A is $(CH_2)_n$, where n=2 to 4, or a unit chosen from formulae (IIa to IIc)

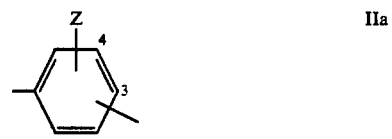

IIa

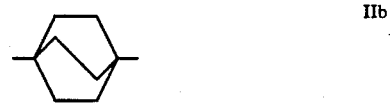

IIb

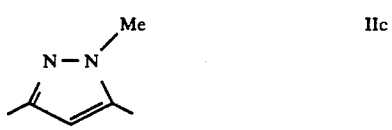

IIc wherein Z=$CH_2Q$, $SO_2NHQ$ or CONHQ, where Q is H, Me, $(CH_2)_nNMe_2(CH_2)_nNHC(=NH)NH_2$ and n=2 to 4), or an acid addition salt or N-oxide thereof.

6 Claims, 4 Drawing Sheets

OTHER PUBLICATIONS

Derwent Abstract Accession No. 92-004475/01, Class J04, JP,A,03-258755, Nov. 19, 1991.

Derwent Abstract Accession No. 85-028995/05, Class C03, JP,A,59-225154, Dec. 18, 1984.

Derwent Abstract Accession No. 76-24468X, Class B05,BE,A,834461, Feb. 2, 1976.

Derwent Abstract Accession No. 77-61836Y, Class BO5,MP,A52-085133, Jul. 15, 1977.

*Chemical Abstracts*, vol. 77, No. 9, issued 1972, col. 2, Abstract No. 616305, CH 520657.

*Chemical Abstracts*, vol. 96, No. 23, issued Jun. 7, 1982, p. 636, col. 1, Abstract No. 199,331 u., CS 193137.

*Chemical Abstracts*, vol. 97, No. 21, issued Nov. 22, 1982, p. 786, col. 1, Abstract No. 181999d CS, 198794.

Braithwaite, A. W. and Baguley, B. C., *Biochemistry*, 1980, vol. 19, pp. 1101-1106.

Denny et al., *Journal of Medicinal Chemistry*, 1979, vol. 22, No. 2, pp. 134-150.

Hurley, L. H., Needham-Van Devanter, D. R., *Acc. Chem. Res.*, 1986, vol. 19, pp. 230-237.

Hurley et al., *Biochemistry*, 1988, vol. 27, pp. 3886-3892

Mitchell et al. *Journal of the American Chemical Society*, 1989, vol. 111, pp. 6428-6429.

Tang et al., *Biochemistry*, 1988, vol. 27, pp. 893-901.

Palmer et al., *Journal of Medicinal Chemistry*, 1990, vol. 33, pp. 112-121.

Pieper et al., *Carcinogenesis*, 1989, vol. 10, pp. 1307-1314.

Finlay et al., *Analytical Biochemistry*, 1984, vol. 139, pp. 272-277.

Garcia et al., *Biochemical Pharmacology*, 1988, vol. 37, No. 16, pp. 3189-3192.

Prakash et al., *Biochemistry*, 1990, vol. 29, pp. 9799-9807.

Wilson et al., *Journal of Medicinal Chemistry*, 1989, vol. 32, pp. 23-30.

AROMATIC MUSTARDS AND AZIRIDINES AND PHARMACEUTICAL USES THEREOF

The present invention relates to novel polybenzamide mustards having anticancer and hypoxia-selective properties, to methods of preparing the novel compounds, and to the use of these compounds as anticancer agents.

BACKGROUND OF THE INVENTION

Alkylating agents are an important class of anticancer drugs, which express their cytotoxic and antitumour effects by forming adducts with cellular DNA.

Bifunctional nitrogen mustard alkylating agents such as chlorantbucil, melphalan, and cyclophosphamide are a major subset of this class of drugs. Their mechanism of antitumour action has been shown to be via interstrand cross-linking of cellular DNA, primarily at guanine N7 sites in runs of guanines in the major groove, which are both the most accessible and the most nucleophilic DNA sites. Because the two alkylating functions on the nitrogen mustard are in such close proximity, cross-linking is limited to DNA sequences which contain two reactive nucleophilic centers within reach of the mustard, with most of the interstrand cross-links being between proximate guanines. Due partly to these spatial restraints, a large proportion of the molecules alkylate DNA only once, forming monoadducts which are primarily genotoxic rather than cytotoxic. A major mechanism of cellular resistance to nitrogen mustards is increased DNA repair of the crosslinks which are formed.

There has been less work on compounds designed to alkylate in the minor groove of DNA, where the most susceptible sites are the N3 of adenine and the exocyclic amino group of guanine, which are the sites targeted respectively by the two best known minor groove alkylating agents CC-1065 (Hurley et al., 1988) and anthrarnycin (Hurley & Needham-VanDevanter, 1986). These compounds are extraordinarily-potent cytotoxins, in spite of forming only monoadducts, possibly because they do not readily induce DNA repair enzymes (Tang et al., 1988). There is also recent evidence, using transcription termination assays with linearized plasmid DNA containing the 420 base pair Pst 1 fragment of exon 2 of the human c-myc oncogene, that two nitrogen mustards (chlorambucil and melphalan) cause termination of transcription preferentially at adenines (at every adenine pair in the melphalan-treated template, and at selected A-G and GA pairs in the chlorambucil-treated template), in spite of the fact that most of the alkylation by these compounds occurs at guanines (Pieper et al., 1989).

For these reasons we have been interested in the development of minor groove-targeted bifunctional alkylating agents as potential antitumour drugs. We report here the design and synthesis of a family of spatially-separated bis-mustards, and studies on interaction with DNA and antitumour properties of a representative compound.

While there have been recent reports on the preparation of bifunctional aniline mustard analogues of the minor groove binding polypyrrole antibiotic distamycin A, we are not aware of any examples of spatially-separated minor groove-targeted mustards. However, a recent report on compounds containing two CC-1065 alkylating units showed that these compounds cross-linked DNA and displayed extraordinary cytotoxic potency (Mitchell et al, 1989).

It was decided to employ aniline mustards as the alkylating moieties in the design of compounds of this invention because of their well-understood alkylation chemistry and because their reactivity can be modulated over a wide range by suitable choice of substituents in the aromatic ring (Palmer et al., 1990). Although there has been little evidence to date of the ability of aniline mustards to alkylate DNA in the minor groove, they have not been designed to target this site. This is despite the fact that the aniline ring of such compounds can itself form part of the minor groove-targeting ligand. The design of was based on the polybenzamide bisquaternary ammonium heterocycles (Denny et al., 1979; Braithwaite and Baguley, 1980), with the dimethylaminomethyl group replacing the terminal quaternary ammonium rings.

SUMMARY OF THE INVENTION

In one aspect, the present invention provides a class of aromatic mustards represented by the general formula (I);

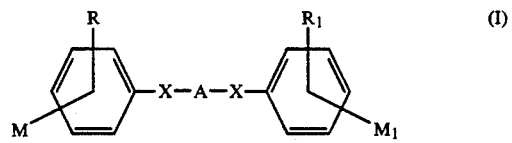

where M and $M_1$ separately represent H, aziridinyl, N(Et)CH$_2$CH$_2$Y or N(CH$_2$CH$_2$Y)$_2$ (where Y is Cl, Br, I or OSO$_2$Me); R and $R_1$ separately represent up to three of H, NO$_2$, aza (ring CH=replaced by N=), CH$_2$Q, SO$_2$NHQ or CONHQ such that at least one of R and $R_1$ is CH$_2$NMe$_2$, (where Q is H, Me, (CH$_2$)$_n$NMe$_2$, (CH$_2$)$_m$NHC(=NH)NH$_2$ and n=0, 2–4 and m=2–4), with the proviso that n may only be 0 when R or $R_1$ is —CH$_2$Q, and Q is —(CH$_2$)$_n$NME$_2$; X represents CONH, NHCO, O, CH$_2$, NH or S; and A is (CH$_2$)$_n$ (where n=2–4) or a unit chosen from formulae (IIa–IIc). In formulae (IIa–IIc), Z=H,CH$_2$Q, SO$_2$NHQ or CONHQ (where Q is H, Me, (CH$_2$)$_p$NMe$_2$, (CH$_2$)$_p$NHC(=NH)NH$_2$ and p=2–4).

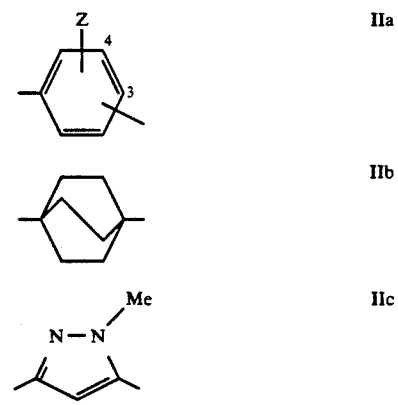

The compounds of formula (I) have cytotoxic and anticancer activity, and are useful as antitumour agents and are particularly useful in the treatment of neoplastic disease states. The compounds of formula (I) form pharmaceutically-acceptable addition salts with both organic and inorganic acids, and these addition salts also form part of the present invention. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic and the like. Certain members of the class of compounds of formula (I), containing tertiary alkyl amines, also form N-oxides of these amines, and these N-oxides also form part of the present invention.

In a second aspect, tile invention provides a method of synthesis of a compound of general formula (I) or of an acid addition salt or N-oxide thereof comprising steps as set out in Schemes 1 to 4 described herein.

In a third aspect, the invention provides a pharmaceutical composition comprising an effective amount of a compound of general formula (I), or an acid addition salt or N-oxide thereof, together with a pharmaceutically acceptable carrier.

In a fourth aspect, the invention provides a method of treatment of cancer in a mammal, comprising the step of administering to a mammal in need of such treatment an anti-tumour effective amount of a compound of general formula (I), or of an acid addition salt or N-oxide thereof.

The compounds of formula (I) and the acid addition salts and N-oxides thereof may be prepared by the processes outlined in Schemes 1–4.

SCHEME 1

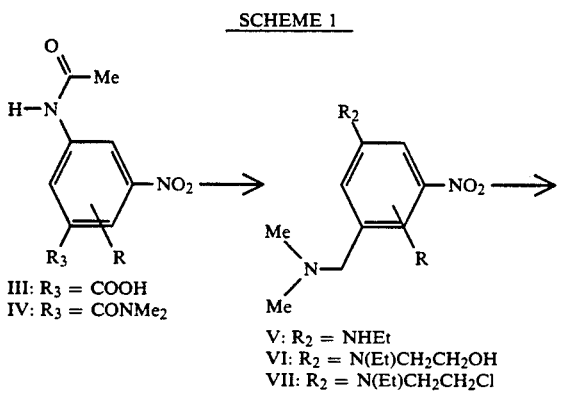

III: $R_3$ = COOH
IV: $R_3$ = CONMe$_2$

V: $R_2$ = NHEt
VI: $R_2$ = N(Et)CH$_2$CH$_2$OH
VII: $R_2$ = N(Et)CH$_2$CH$_2$Cl

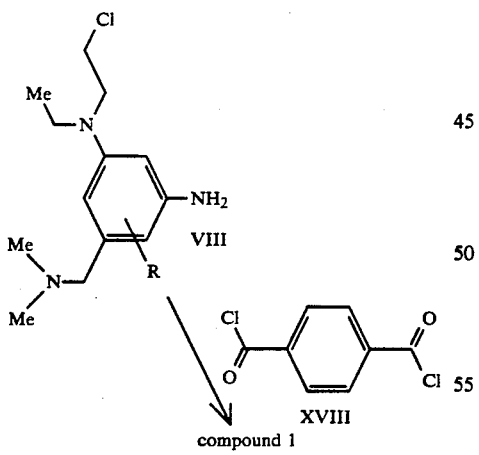

compound 1

In Scheme 1, R and Z are as defined for formulae I and IIa, but are not nitro. Reaction of substituted 3-acetamido-5-nitrobenzoic acids (III) with dimethylamine gives substituted N,N-dimethyl-[3-acetamido-5-nitro]benzamides (IV), which undergo reduction with BH$_3$.S(CH$_3$)$_2$ complex to afford substituted N,N-dimethyl-[3-(N-ethylamino-5-nitro]-benzylamines (V). Treatment of these with excess oxirane in aqueous acetic acid/THF at room temperature gives the substituted N-2-hydroxyethyl derivatives (VI), and mesylation of these followed by treatment with LiCl provides the substituted N-2-chloroethyl derivatives (VII) Reduction of the nitro group of these with stannous chloride/conc.HCl gives the corresponding air-sensitive substituted amines (VIII), which can be reacted with 1,4-benzenedicarbonyl dichlorides (XVIII) (or similar 1,3-benzenedicarbonyl dichlorides) to give the desired compounds of formula (I).

SCHEME 2

R
[structure XVI]
NH$_2$
Me
N
Me

Z
Cl
O
O
OMe
XVII

R
H   Z
N
Me
N   O   R$_2$
Me

IX: $R_2$ = OMe
X: $R_2$ = OH

↓ VIII compound 2

In Scheme 2, R and Z are as defined for formulae (I) and (IIa), but are not nitro. Reaction of 3-(N,N dimethylaminomethyl)-anilines (XVI) with methoxycarbonylbenzenecarbonyl chlorides (XVII) give esters (IX), which can be selectively hydrolysed with an exact equivalent of base to the acids (X), which can be reacted with the amines (VIII) to give the desired compounds of formula (I).

SCHEME 3

Me
N   R$_3$
O$_2$N
R

XI: $R_3$ = OH
XII: $R_3$ = Cl

-continued
SCHEME 3

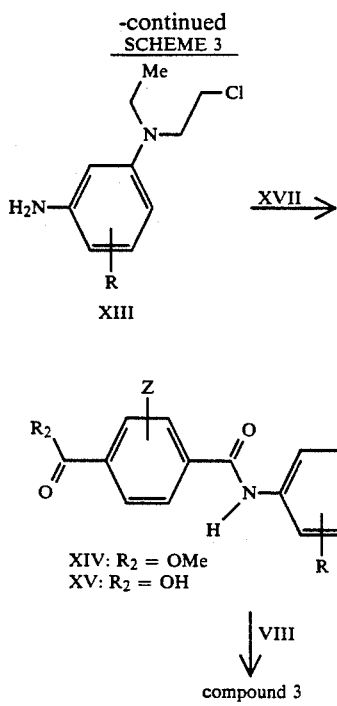

In Scheme 3, R and Z are as defined for formulae (I) and (IIa), but are not nitro. Reaction of alcohols (XI) with MsCl/LiCl gives the mustards (XII), which can be reduced under acidic conditions to the amines (XIII). These can be coupled with methoxycarbonylbenzenecarbonyl chlorides (XVII) to give esters (XIV), which on mild basic hydrolysis yield the acids (XV). These can be coupled with suitable amines (e.g. amines VIII) to give the desired compounds of formula (I).

SCHEME 4

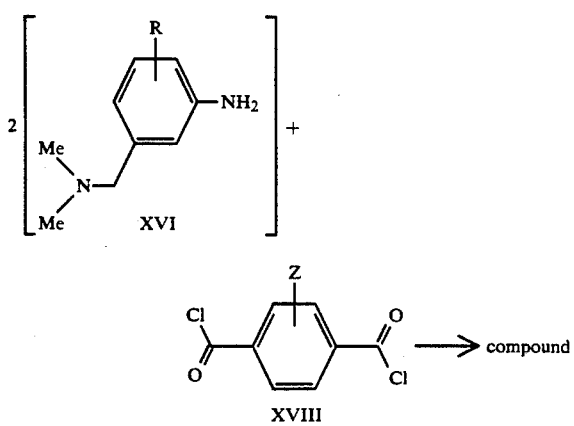

In Scheme 4, R and Z are as defined for formulae (I) and (IIa), but are not nitro. Direct reaction of suitable amines (e.g. XVI) with suitable benzenedicarbonyl chlorides (e.g. XVIII) yield the desired compounds of formula (I).

DESCRIPTION OF THE INVENTION

Figure 2:
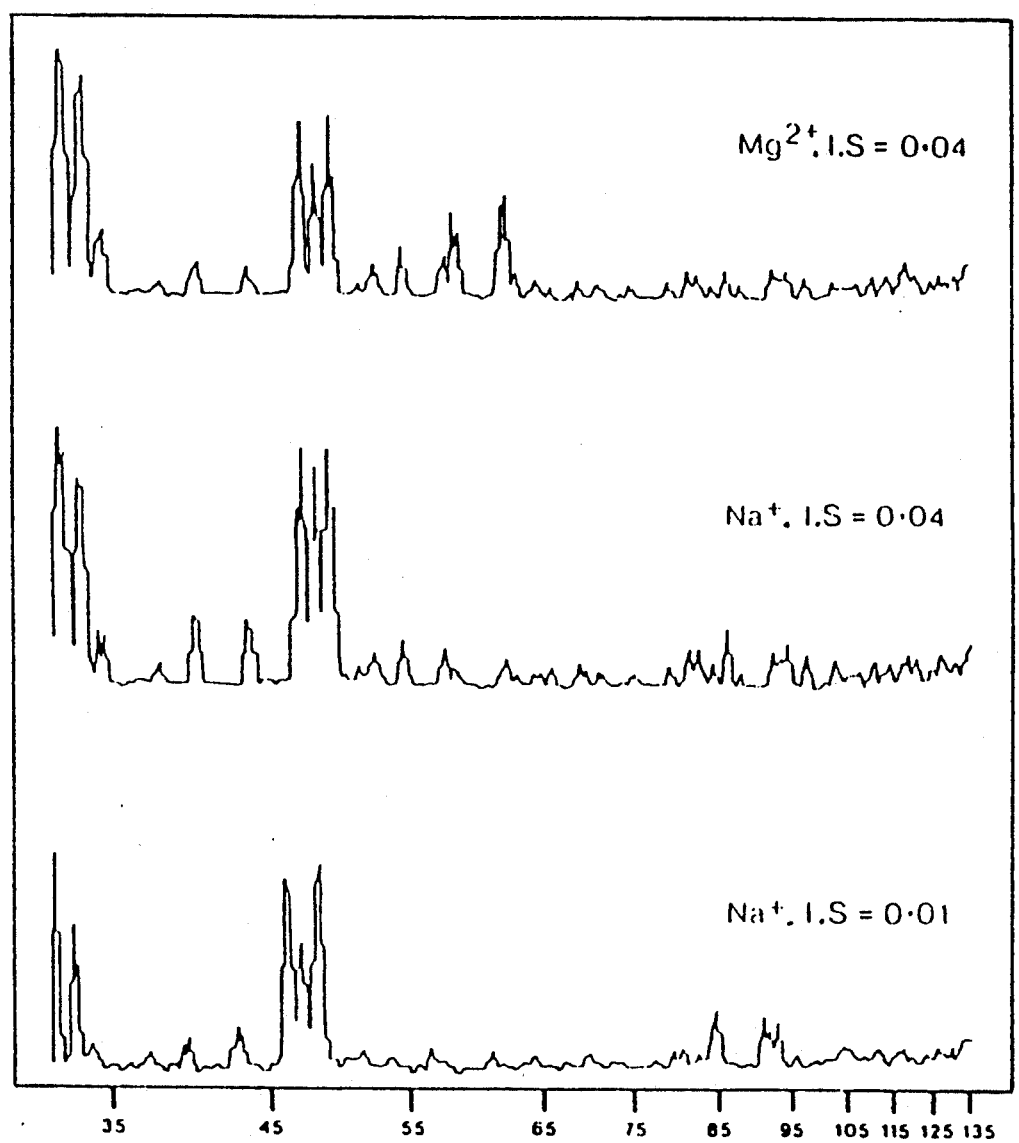
Figure 3:
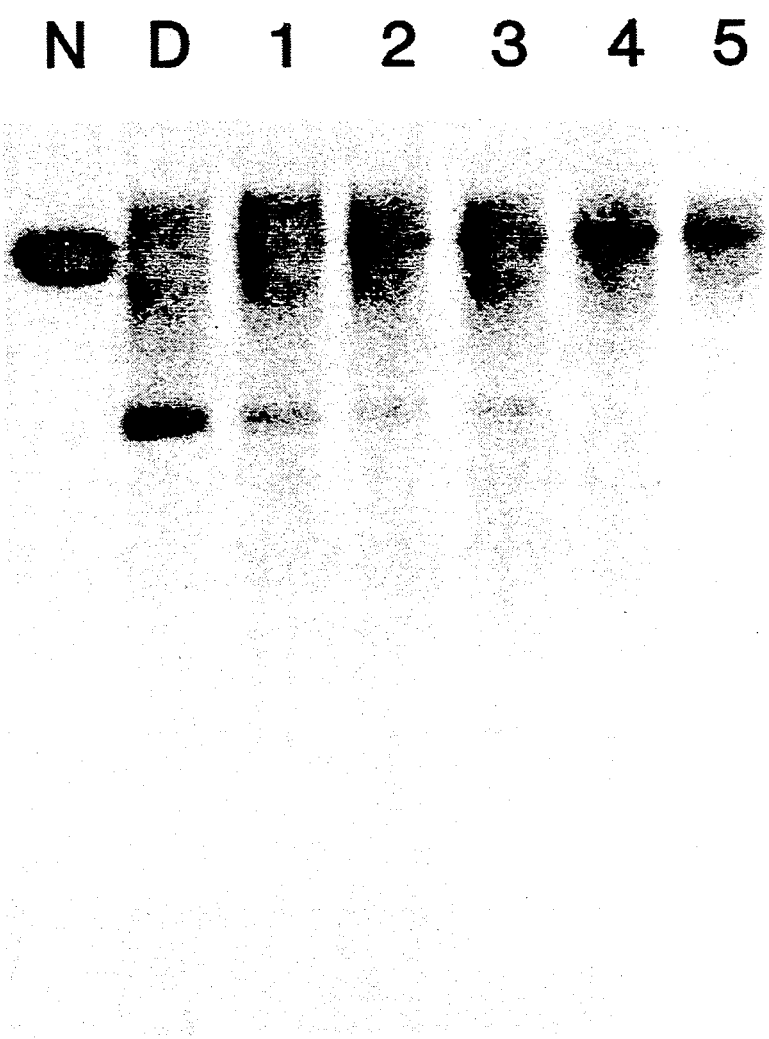
Figure 4:

The invention will now be described by reference to the following non-limiting examples, and to the figures, in which:

FIG. 1 represents an autoradiograph off strand cleavage patterns obtained from the drug-treated 3'-end labelled EcoRf/BamHI fragment of pBR322 DNA. The lanes correspond to control DNA samples in the presence of 30 mM Na+ (lane 1) and 10 mM $Mg^{2+}$ (lane 2), and drug-treated DNA in the presence of 30 mM Na+ (lane 3 ) and 10 mM $Mg^{2+}$ (lane 4 ) (ionic strength=0.04 );

FIG. 2 shows densitometer scans of strand cleavage patterns obtained using drug treated DNA in 0.01 SHE buffer in the presence of: no salt (bottom panel), 30 mM Na+ (middle panel) and 10 mM $Mg^{2+}$ (top panel). IS=ionic strength of the reaction mixture;

FIG. 3 shows an autoradiograph obtained from crosslinking experiments using 3'-end labelled EcoRl digested linear pBR322 DNA incubated with compound 1, using drug/bp ratios of 0.02, 0.04, 0.06, 0.08 and 0.10 (lanes 1-5 respectively). Lane D is control denatured DNA subjected to identical denaturing conditions to the drug-treated samples, and lane N is control native DNA not subjected to denaturation; and FIG. 4 shows results of unwinding of closed circular superhelical plasmid pBR322 incubated With compound 1 at drug/bp ratio 0.0, 0.10, 0.15, 0.20, 0.25, 0.30, 0.35 and 0.40 (numbered 1 to 8 in the figure).

Table 1 gives physicochemical data for six compounds within the general formula (I), representative of it, and preparable by the processes of the invention.

TABLE 1

Physicochemical data for representative compounds within general formula (1) [diag]

| No. | R | M | $R_1$ | $M_1$ | mp | formula | analyses |
|---|---|---|---|---|---|---|---|
| 1 | $CH_2NMe_2$ | $N(Et)CH_2CH_2Cl$ | $CH_2NMe_2$ | $N(Et)CH_2CH_2Cl$ | 200 | $C_{34}H_{46}Cl_2N_6O_2.2H_2O$ | C, H, N, Cl |
| 2 | $CH_2NMe_2$ | $N(Et)CH_2CH_2Cl$ | $CH_2NMe_2$ | H | 162-165 | $C_{30}H_{38}ClH_5O_2$ | C, H, N, Cl |
| 3 | $CH_2NMe_2$ | $N(Et)CH_2CH_2Cl$ | H | H | 186-189 | $C_{27}H_{31}ClN_4O_2$ | C, H, N, Cl |
| 4 | $CH_2NMe_2$ | $N(Et)CH_2CH_2Cl$ | H | $N(Et)CH_2CH_2Cl$ | >250 | $C_{31}H_{39}Cl_2N_5O_2$ | C, H, N, Cl |
| 5 | H | $N(Et)CH_2CH_2Cl$ | $CH_2NMe_2$ | H | 160-161 | $C_{27}H_{31}ClN_4O_2$ | C, H, N, Cl |
| 6 | $CH_2NMe_2$ | H | $CH_2NMe_2$ | H | >300 | $C_{26}H_{30}N_4O_2.2HCl$ | C, H, N, Cl |

The following Examples illustrate the preparation of compounds respective of the general formula (I).

EXAMPLE 1

Synthesis of bis-N, N'-[3-(N-(2-chloroethyl)-N-ethylamino)-5-(N,N-dimethylaminomethyl) phenyl]-1,4-benzenedicarboxamide (compound 1 of Table 1) by the method of Scheme 1.

1,1-Carbonyldiimidazole (5.42 g, 33.48 mmol) was added in portions to a stirred solution of 3-acetamido-5-nitrobenzoic acid (III; R=H) (Larsen et al., 1956) (5 g, 22.32 mmol) in dry DMF (20 mL) at room temperature. The mixture was then heated at 40° C. for 30 min, cooled to 10° C. and treated with a solution of dimethylamine (40% in water, 5 mL, 44.64 mmol). The mixture was heated at 40° C. for 30 min, solvent was then removed under reduced pressure and the residue was worked up to give crude N-[5-nitro-3-(N,N-dimethylaminocarbonyl)]phenylacetamide (IV; R=H) (3.95 g, 70%), mp (MeOH) 193°-196° C. $_{max}$ 1705

(CON(CH$_3$)$_2$), 1625 (COCH$_3$), 1515 cm$^{-1}$ (NO$_2$). $^1$H NMR (CD$_3$SOCD$_3$) 2.11 (s, 3H, COCH$_3$), 3.37 (s, 6H, N(CH$_3$)$_2$)), 7.87 (dxd, J$_1$=2.0 Hz, J$_2$=1.3Hz, 1H, H-2), 7.96 (m, 1H, H-4), 8.59 (m, 1H, H-6), 10.55 (s, 1H, NH). $^{13}$C NMR 24.10 (COCH$_3$; 38.94 (N(CH$_3$)$_2$); 113.63 (C-2); 115.82 (C-4); 122.81 (C-6); 138.22 (C-1); 140.45 (C-3); 147.83 (C-5); 167.72 (CON(CH$_3$)$_2$); 169.30 (COCH$_3$); 251 (M, 56%), 250 (M-H, 21); 209 (79), 165 (50), 91(29), 72(31), 43(100). Anal. Found: C, 63.1; H, 5.3; N, 17.0%. C$_{11}$H$_{13}$N$_3$O$_4$ requires C, 62.6; H, 5.2; N, 16.7%.

A stirred solution off the above acetamide (Iv; R=H) (1 g, 4.26 mmol) in dry THF (20 mL) was treated slowly with borane-THF complex (2 mL). After stirring for 12h at room temperature, more borane-THF complex (3 mL) was added and the mixture was refluxed for 1h, then cooled and acidified with dilute aqueous HCl. Volatiles were evaporated under reduced pressure, and the aqueous layer was basified with aqueous NaOH (10%) and extracted with CH$_2$Cl$_2$ to give the crude product. Chromatography on silica gel and elution with EtOAc/hexanes (3:7) gave N,N-dimethyl-[3 -(Nethylamino) -5-nitro]benzylamine (V; R=H) (0.28 g, 30%), mp (benzene/hexanes) 83°-86° C. (orange prisms). $_{max}$ 1535 (NO$_2$), 1325 cm$^{-1}$ (CN). $^1$H NMR (CDCl$_3$) 1.31 (t, J=7.2 Hz, 3H, CH$_2$CH$_3$), 2.57 (s, 6H, N(CH$_3$)$_2$), 3.24 (qxd, J$_1$=7.2 Hz, J$_2$=5.2 Hz, 2H, CH$_2$CH$_3$), 3.94 (s, 2H, CH$_2$N), 4.10 (t, J=5.2 Hz, 1H, NH), 6.88 (m, 1H, H-2), 7.41 (m, 1H, H-4 ), 7.44 (m, H-6). $^{13}$C NMR 14.44 (CH$_2$CH$_3$); 38.36 (NCH$_2$); 50.43 (NCH$_3$); 67.23 (CH$_2$N); 106.62 (C-4); 114.53 (C-6); 122.26 (C-2); 133.34 (C-5); 149.03 (C-1); 149.41 (C-3); 223 (M, 8%), 180(M—C$_2$H$_5$N, 100), 134(17), 58(62). In similar reductions using the borane.dimethylsulfide complex, yields of 70% were obtained.

A mixture of the above N-ethyl derivative (V; R=H) (0.3 g,. 1.35 mmol) and excess oxirane (1 mL) in glacial AcOH/THF (1:1, 20 mL) was stirred at room temperature for 72h. Solvents were removed under reduced pressure, and the residue was chromatographed on silica gel. Elution with EtOAc gave N,N-dimethyl -[3 -(N-ethyl -N-(2 -hydroxyethyl)amino) -5-nitro]benzylamine (VI; R=H) (0.15 g, 42%) s an orange solid, top. (CH$_2$Cl$_2$/hexanes) 102-°104° C. $_{max}$ 3525 (OH), 1530 (NO$_2$), 1325 (arylCN) cm$^{-1}$. $^1$H NMR (CDCl$_3$) 1.22 (t, J=7.1 Hz, 3H, CH$_2$CH$_3$) 2.58 (s, 6H, N(CH$_3$)$_2$), 3.51 (q, J=7.1 Hz, 2H, NCH$_2$CH$_3$), 3.56 (t , J=5.8 Hz, 2H, NCH$_2$CH$_2$OH), 3.86 (br s, 2H, CH$_2$OH), 3.95 (br s, 2H, CH$_2$N(CH$_3$)$_2$), 7.05 (br s, 1H, H-2), 7.41 (br s, 1H, H-4), 7.56 (t, J=2.1 Hz, 1H, H-6). $^{13}$C NMR 11.70 (CH$_2$CH$_3$); 45.69 (NCH$_2$H$_3$); 50.63 (N(CH$_3$)$_2$); 52.40 (NCH$_2$CH$_2$OH); 60.17 (CH$_2$OH); 67.65 (CH$_2$N(CH$_3$)$_2$); 106.65 (C-4); 113.38 (C-6); 121.59 (C-6); 133.40 (C-1); 148.74 (C-5); 149.34 (C-3). m/z 267 (M, 0.3%); 236(M—CH$_2$OH,100), 192(27), 58(61). (Found: C, 53.4; H, 8.3; N, 14.0%. C$_{13}$H$_{21}$N$_3$O$_3$.1.5H$_2$O requires C, 53.0; H, 8.2; N, 14.3%).

A solution of the above N-hydroxyethyl derivative (VI: R=H) (0.2 g, 0.75 retool) in CH$_2$Cl$_2$ (5 mL) containing NEt$_3$ was treated with methanesulfonyl chloride (0.2 mL, 2.62 mmol ), followed by excess LiCl in DMF (5 mL). Workup gave N,N-dimethyl -[3 -(N- ethyl -N-(2 -chloroethyl)amino )-5 -nitro ]benzylamine (VII; R=H) (0.11 g, 52%), mp (CH$_2$Cl$_2$/hexane) 169°-172° C. $_{max}$ 1525 (NO$_2$) 1320 (CN), 760 cm$^{-1}$ (CH$_2$Cl). $^1$H NMR (CDCl$_3$) 1.25 (t, J=7.1 Hz, 3H, CH$_2$CH$_3$), 3.61 (q, J=7.1 Hz, 2H, CH$_2$CH$_3$), 3.78 (m, 2H, NCH$_3$.83 (m, 2H, NCH$_2$), 4.20 (s, 2H, CH$_2$N(CH$_3$)$_2$), 7.44 (m, 1H, H-2), 7.53 (m, 1H, H-4), 7.84 (dxd, J$_1$=1.3 Hz, J$_2$=2.4 Hz, 1H, H-6). $^{13}$C NMR 11.92 (CH$_2$CH$_3$); 41.22 (CH$_2$CH$_3$); 42.62 (N(CH$_3$)$_2$); 46.0 9 (CH$_2$Cl); 52.13 (NCH$_2$); 61.19 (CH$_2$N(CH$_3$)$_2$); 107.27 (C-4); 111.68 (C-6); 119.17 (C-2); 131.49 (C-1); 149.18 (C-5); 149.64 (C-3). m/z 285 (M, 15%), 242 (M-CH$_2$NCH$_3$) 86), 236 (M-CH$_2$Cl, 62), 193 (242—CH$_2$Cl, 37), 58(100). (Found: C, 48.0; H, 6.8; N, 12.5; Cl, 13.5.C$_{13}$H$_{20}$N$_3$O$_2$Cl.2H$_2$O requires C, 48.4; H, 7.5; N, 13.0; Cl, 11.0%).

A solution of the above mustard (VII; R=H) (0.57 g, 2.00 mmol) in conc.HCl (5 mL) was stirred vigorously while tin(II) chloride (1.80 g, 8.00 mmol) was added in portions. The solution was refluxed for 2h, cooled, diluted with water, washed with EtOAc, basified with conc. ammonia to pH 8-9, extracted with CH$_2$Cl$_2$, and worked up to give 3-[N-(2-chloroethyl) -N-ethylamino]-5-[(N,N-dimethylamino)methyl]aniline (VIII; R=H) (0.34 g, 67%) as an oil, which was used directly. $^1$H BrMR (CDCl$_3$) 1.16 (m, 3H, CH$_2$CH$_3$), 2.74 (s, 6H, N(CH$_3$)$_2$), 3.35 (m, 2H, CH$_2$CH$_3$), 3.62 (s, 4H, NCH$_2$CH$_2$Cl), 3.94 (s, 2H, CH$_2$N(CH$_3$)$_2$) 6.22 (br s, 3H, H-2,4,6).

1,4-Benzenedicarbonyl dichloride (XVIII; Z=H) (0.14 g, 0.67 mmol) was added in one portion to a stirred solution of the above amine (VIII) (0.34 g, 1.33 retool) in CH$_2$Cl$_2$ (5 mL), and the mixture was stirred at room temperature for 30 min. The solvent was removed under reduced pressure and the residue was dissolved in water, basified with conc. ammonia to pH 8-9 and extracted with CH$_2$Cl$_2$. Workup gave the free base of bis-N,N'-[3-(N-(2-chloroethyl)-N-ethylamino)-5-(N,N-dimethylaminomethyl) phenyl]-1,4-benzenedicarboxamide (1) (0.31 g, 72%) as a pale yellow solid, mp (CH$_2$Cl$_2$/ether) 200° C. (dec). $_{max}$ 1645 (CO), 1610 (C-C), 1340 (CN) 1155, 715 cm$^{-1}$ (CH$_2$Cl). $^1$H NMR (of diHCl salt (CD$_3$SOCD$_3$) 1.14 (t, J=6.9 Hz, 6H, CH$_2$CH$_3$), 2.71 (d, J=4.7 Hz, 12H, N(CH$_3$)$_2$), 3.46 (g, J=6.9 Hz, 4H, NCH$_2$CH$_3$), 3.65 (t, J=6.7 Hz, 4H, CH$_2$Cl), 3.80 (t, J=6.7 Hz, 4H, NCH$_2$CH$_2$Cl), 4.18 (d, J=5.1 Hz, 4H, CH$_2$N(CH$_3$)$_2$), 6.89 (s, 2H, H-4', 4''), 7.23 (s, 2H, H-2', 2''), 7.37 (s, 2H, H-6', 6''), 8.13 (s, 4H, H-2,3,5,6), 10.47 (s, 2H, NH), 10.90 (br s, 2H, HCl). $^{13}$C NMR 12.51 (CH$_2$CH$_3$); 40.76 (CH$_2$Cl); 45.09 (N(CH$_3$)$_2$; 45.67 (NCH$_2$ CH$_3$); 52.36 (NCH$_2$CH$_2$Cl); 64.44 (CH$_2$N(CH$_3$)$_2$); 103.09 (C-4', 4''); 109.10 (C-2', 2''); 109.17 (C-6', 6''); 127.51 (C-2,3,5,6); 137.92 (C-5', 5''); 139.17 (C-1',1''); 139.74 (C-3',3''); 147.87 (C-1,4); 164.92 (CO). Mass spectrum (of free base) m/z 640(M, 28%), 105(50), 58(100). (Found: C, 60.9; H, 7.2; N, 11.9; Cl, 12.7.C$_{34}$H$_{46}$N$_6$O$_2$Cl$_2$.2H$_2$O requires C, 60.3; H, 7.9; N, 12.4; Cl, 10.5%).

EXAMPLE 2

Synthesis of N-[3-(N-(2-chloroethyl)-N-ethylamino) -5 -(N,N -dimethylaminomethyl)phenyl]-N$^1$-[(3-(N,N-dimethylaminomethyl) phenyl]-1,4 -benzenedicarboxamide (compound 2 of Table 1) and N-[3-(N-(2-chloroethyl)-N-ethylamino) -5-(N,N-dimethylaminomethyl)phenyl]-N$^1$-phenyl-1,4-benzenedicarboxamide (compound 3 of Table 1) by the method of Scheme 2.

Equimolar amounts of 3 -(N,N-dimethylaminomethyl)aniline (XVI; R=H) (Stedman, E. J. Chem. Soc. 1927, 1902) and 4-(methoxycarbonyl) benzenecarbonyl chloride (XvII; Z=H) were reacted together in pyridine at 0 ° C., to give methyl 4-[3 -(N,N-dimethylaminomethyl)phenyl]carbamoylbenzene-carboxylate (IX; R=Z=H) (73%), mp (diisopropyl ether) 108°–109 °C. $^1$H NMR (CD$_3$SOCD$_3$) 10.42 (s, 1 H, CONH), 8.13 (s, 4 H, H-2',H-3'), 7.75 (s, 1H, H-2), 7.70 (d, J=8.2 Hz, 1 H, H-6), 7.30 (t, J=8.2 Hz, 1 H, H-3), 7.04 (d, J=8.2 Hz, 1 H, H-4), 3.97 (s, 3H, COOCH$_3$), 3.40 (s, 2 H, CH$_2$), 2.18 (s, 6 H, N (CH$_3$)$_2$). Anal.(C$_{18}$H$_{20}$N$_2$O$_3$) C, H, N.

A solution of ester (IX; R=Z=H) (5.30 g, 17 mmol) in MeOH (10 mL) was treated with one equivalent of NaOH (17.0 nil of 1.0 N aqueous solution), and the mixture was heated until the MeOH had boiled off, and for 1 h under reflux, then cooled and filtered. Exact neutralisation (with 17.0 mL of 1.0 N aqueous HCl) followed by refrigeration yielded 4-[3-(N,N-dimethylaminomethyl) phenyl]carbamoylbenzene-carboxylic acid (X; R=Z=H) (4.73 g, 93%), mp (MeOH/EtOAc) 209°–210 °C. $^1$H NMR (CD$_3$SOCD$_3$) 10.41 (s, 1 H, NH), 8.07 (d, J=7.0 Hz, 2 H, H-2', 6'), 8.02 (d, J=7.0 Hz, 2 H, H-3',5'), 7.82 (s, 1 H, H-2), 7.72 (d, J=8.05 Hz, 1 H, H-4), 7.33 (U, J=7.8 Hz, 1 H, H-5), 7.09 (d, J=7.6 H z, 1 H, H -6), 3.61 (s, 2 H, CH$_2$), 2.32 (s, 6 H, N(CH$_3$)$_2$). Anal. (C$_{17}$H$_{18}$N$_2$O$_3$) C, H, N.

An ice cold solution of: (X; R=Z=H) (0.70 g, 2.35 retool) in dry DMF (5 mE) containing 1-methylimidazole (0.21 g, 2.56 mmol) was added to solid (VIII; R=H) (0.61 g, 2.38 mmol) contained in a pre-cooled flask. The mixture was stirred until homogeneous, and then treated dropwise with diethyl cyanophosphonate (93%, 0.43 g, 2.45 retool) at 0 °C. The mixture was stirred at 25 °C. for 1.5 h, then diluted with a large excess of 0.5 N Na$_2$CO$_3$ and the resulting solid collected and extracted into CH$_2$Cl$_2$. The CH$_2$Cl$_2$ solution was washed twice with water and evaporated, and the residue was chromatographed on a short column of alumina (activity II-III). Elution with EtOAc gave N-[3-(N-(2-chloroethyl)-N-ethylamino)-5-(N,N-dimethylaminomethyl) phenyl]-N$^1$- [(3-(N,N-dimethylaminomethyl) phenyl]-1,4-benzenedicarboxamide (2) (0.59 g, 47%), mp (EtOAc/petroleum ether) mp 162°–165 °C. $^1$H NMR (CDCl$_3$) 8.27 & 8.15 (2×s, 2 H, CONH, CONH), 7.85 (s, 4 H, H-2',3',5',6'), 7.67 (d, J=7.9 Hz, 1 H, H-2''), 7.56 (s, 1 H, H-6''), 7.31 (t, J=7.8 Hz, 1 H, H-3''), 7.11 (s, 1 H, H-4''), 6.79 (s, 1 H, H-4), 6.45 (s, 1 H, H-6), 3.71 (s, 4 H, NCH$_2$CH$_2$Cl), 3.44 (q, J=7.0 Hz, 2 H, NCH$_2$CH$_3$), 3.42 & 3.45 (2×s, 2 H, 2 × CH$_2$N (CH$_3$)$_2$ ), 2.23 (s, 12 H, 2×N(CH$_3$)$_2$), 1.19 (t, J=7.0 Hz , 3 H, NCH$_2$CH$_3$). Anal. (C$_{30}$H$_{38}$ClN$_5$O$_2$) C, H, N, Cl.

Similar reaction of 4-phenylcarbamoylbenzenecarboxylic acid and amine (VIII; R=H) gave N-[3-(N-(2-chloroethyl)-N-ethylamino) -5-(N,N-dimethylaminomethyl) phenyl]-N$^1$-phenyl-1,4-benzenedicarboxamide (3) (52%), mp (EtOAc/petroleum ether) 186°–189 °C. $^1$H NMR (CDCl$_3$) 8.08, 7.98 (2×s, 2 H, CONH, CONH), 7.90 (s, 4 H, H-2',3',5',6'), 7.67 (d, J=7.8 Hz, 2 H, H-2'', 6''), 7.38 (t, J=7.6 Hz, 2 H, H-3'', 5''), 7.25 (s, 1 H, H-2), 7.18 (t, J=7.4 Hz, H-4''), 6.75 (s, 1 H, H-4), 6.46 (s, 1 H, H-6), 3.66 (s, 4 H, NCH$_2$CH$_2$Cl), 8.44 (q, J=7.0 Hz, 2 H, NCH$_2$CH$_3$), 3.36 (s, 2 H, CH$_2$N(CH$_3$)$_2$), 2.24 (s, 6 H, N(CH$_3$)$_2$), 1.21 (t, J=7.0 Hz, 3 H. NCH$_2$CH$_3$). Anal.(C$_{27}$H$_{31}$ClN$_4$O$_2$) C, H, N, Cl.

EXAMPLE 3

Synthesis of N-[3-(N-(2-chloroethyl)-N-ethylamino)-5-(N,N-dimethylaminomethyl)phenyl]-N$^1$-[3-(N-(2-chloroethyl) -N-ethylamino) phenyl]-1,4-benzenedicarboxamide (compound 4 of Table 1) and N-[3-(N-(2-chloroethyl)-N-ethylamino) phenyl]-N$^1$-[3-(N,N-dimethylaminomethyl)phenyl]-1,4-benzenedicarboxamide (compound 5 of Table 1) by the method of Scheme 3.

A solution of N-ethylaniline (13.3 g, 80 mmol) in THF (50 nmL) and AcOH (50 niL) was treated with oxirane (15 mL, 0.3 mol), and the mixture was stirred at 20 °C. for 36 h. Additional oxirane (15 mL) was then added, and the mixture was stirred at 20 °C. for an additional 36 h. Solvent was then removed under reduced pressure, and the residue was partitioned between CH$_2$Cl$_2$ and 1N aqueous Na$_2$CO$_3$. The residue obtained from workup of the organic layer was chromatographed on SiO$_2$ (EtOAc/petroleum ether, 1:3) to give N-ethyl-N-(2-hydroxyethyl)-3-nitroaniline (XI; R=H) (12.3 g, 75%), mp (benzene/petroleum ether) 43 °C. $^1$H NMR (CDCl$_3$) 7.53 (t, J=2.3 Hz, 1 H, H-2), 7.49 (dd, J=8.2, 2.0 Hz, 1 H, H-4 ), 7.30 (dd, J=8.4, 8.2 Hz, 1 H, H-5), 7.01 (dd, J=8.4, 2.6 Hz, 1 H, H-6), 3.83 (br s, 1 H, CH$_2$OH), 3.54 (t, J=5.9 Hz, 2 H, NCH$_2$CH$_2$OH), 3.49 (q, J=7.1 Hz, 2 H. NCH$_2$CH$_3$), 1.72 (br s, 1 H, OH), 1.21 (t, J=7.1 Hz, 3 H, CH$_3$O. Anal. (C$_{10}$H$_{14}$N$_2$O$_3$) C,H,N.

A stirred solution of the above alcohol (XI; R=H) (4.0 g, 19 mmol) in CH$_2$Cl$_2$ (35 mL) containing NEt$_3$ (2.91 mL, 21 mmol) was treated dropwise at 0 °C. with methanesulfonylchloride (1.62 mL, 21 mmol). After being stirred at 0 °C. for a further 30 min and at 20 °C. for 30 min, the reaction mixture was diluted with CH$_2$Cl$_2$ (35 mL) and washed successively with 1N HCl, 1N Na$_2$CO$_3$ and saturated NaCl, and worked up to give the crude mesylate, which was immediately treated with LiCl (2 g) in dry DMF (20 mL) at 75° C. for 30 min. Removal of excess solvent under reduced pressure, and chromatography of the residue on SiO$_2$ (EtOAc/petroleum ether, 1:4 ) gave N-(2-chloroethyl)-N-ethyl-3-nitroaniline (XII; R=H) (3.58 g, 82%) as yellow prisms, mp (petroleum ether) 56°–57 °C. $^1$H NMR (CDCl$_3$) 7.51 (dd, J=7.9, 1.9 Hz, 1 H, H-4), 7.48 (t, j=2.4 Hz, 1 H, H-2), 7.32 (m, 2 H, H-5), 6.95 (dd, J=8.4, 2.7 Hz, H-6), 3.70 (m, 2 H, NCH$_2$CH$_2$Cl), 3.64 (m, 2 H, CH$_2$Cl), 3.50 (q, J=7.1 Hz, 2 H, NCH$_2$CH$_3$), 1.22 (t, J=7.1 Hz, 3 H, CH$_3$). Anal.(C$_{10}$H$_{13}$ClN$_2$O$_2$) C,H,N,Cl.

A solution of the above nitro mustard (XII; R=H) (2.51 g, 11 mmol) in 12 N HCl (25 mL) was treated portionwise at 25 °C. with SnCl$_2$.2H$_2$O (9.9 g, 44 mmol), heated on a steam bath at 90° C. for 1 h, then evaporated to dryness under reduced pressure. The residue as shaken vigorously With a mixture of CH$_2$Cl$_2$, 2 N NH$_4$OH and ice, and filtered through a celite pad. Workup of the organic layer gave essentially pure 3-[N-(2-chloroethyl) -N-ethylamino]aniline (XIII; R=H) (1.92 g, 88%) as an oil, which was used immediately.

A stirred solution of the amine (XIII; R=H) (2.38 g, 12 mmol) in CH$_2$Cl$_2$ (30 mL) containing NEt$_2$ (1.80 mL, 13 mmol) was treated dropwise at 0 °C. with a solution of 4-methoxycarbonylbenzenecarbonyl chloride (XVII; Z=H) (2.18 g, 11 mmol) in CH$_2$Cl$_2$ (10 mL). After being stirred for a further 15 min at 0° C. and for 15 min at 25° C., the mixture was washed with 1 N Na$_2$CO$_3$ and water, and the residue from the organic layer was chromatographed on SiO$_2$ (CH$_2$Cl$_2$) to give methyl 4-[3-(N-(2-chloroethyl)-N-ethylamino)phenyl]carbamoylbenzenecarboxylate (XIV; R=Z=H) (3.36 g, 85%), mp (benzene/petroleum ether) 111°-112° C. $^1$H NMR (CD$_3$SOCD$_3$) 10.25 (s, 1 H, CONH), 8.09 (m, 4 H, H-2',3',5',6'), 7.16 (d, J=1.8 Hz, 1 H, H-2), 7.15 (m, 2 H, H-4,H-6)E 6.49 (m, 1 H, H-5), 3.93 (s, 3 H, COOCH$_3$), 3.73 (t, J=7.1 Hz, 2 H, NCH$_2$CH$_2$Cl), 3.61 (t, J=7.1 Hz, 2 H, CH$_2$Cl), 3.41 (t, J=7.0 Hz, 2 H, NCH$_2$CH$_3$), 1.12 (t, J=7.0 Hz, 3 H, CHs). Anal. (C$_{19}$H$_{21}$ClN$_2$O$_3$) C,H,N,Cl.

A suspension of (XIV; R=Z=H) (2.88 g, 8 mmol) in MeOH (100 mL) containing KOH (5.6 g) was stirred at 25° C. until homogeneous, and then for a further 5 h. The mixture was diluted with water, filtered, and acidified with AcOH to give 4-[3-(N-(2-chloroethyl)-N-ethylamino) phenyl]carbamoylbenzenecarboxylic acid (XV; R=Z=H) (2.08 g, 75%), mp (EtOAc) 203° C. (dec.). $^1$H NMR (CD$_3$SOCD$_3$) 13.3 (br s, 1 H, COOH), 10.21 (s, 1 H, CONH), 8.05 (q, J=8.50, 4 H, H-2',3',5'6'), 7.16 (m, 3 H, H-2,4,6 ), 6.48 (m, 1 H, H-5), 3.72 (t, J=7.1 Hz, 2 H, NCH$_2$CH$_2$Cl), 3.60 (t, J=7.1 Hz, 2 H, CH$_2$Cl), 3.40 (g, J=7.0 Hz, NCH$_2$CH$_3$)-, 1.12 (t, J=7.0 Hz, 3 H, CH$_3$). Anal. (C$_{18}$H$_{19}$ClN$_2$O$_3$) C,H,N,Cl.

Reaction of acid (XV; R=Z=H) and amine (VIII; R=H) by the method outlined in Example 2 gave N-[3-(N-(2-chloroethyl) -N-ethylamino)-5-(N,N-dimethylaminomethyl)phenyl -N$^1$-[3-(N-(2- chloroethyl)-N-ethylamino)phenyl]-1,4-benzenedicarboxamide (4) (61%) mp (EtOAc/petroleum ether) >250° C. $^1$H NMR (CDCl$_3$) 8.11 , 8.07 (2×s, 2 H, CONH, CONH), 7.87 (s, 4 H, H-2',3',5',6'), 7.24 (s, 2 H, H-2,2''), 7.20 (m, 1 H, H-5''), 6.87 (d, J=7.8 Hz, 1 H, H-4''), 6.77 (s, 1 H, H-4 ), 6.50 (dd, J=8.3, 2.4 Hz, 1 H, H-6''), 6.44 (s, 1 H, H-6), 3.62 (s, 8 H, 2×CH$_2$CH$_2$Cl), 3.44 (2×q, J =7.0 Hz, 4 H, 2×NCH$_2$CH$_3$), 3.36 (s, 2 )(CH$_2$N(CHs)$_2$), 2.23 (s, 6 H, N(CH$_3$)$_2$.), 1.99 (2×t, J=7.0 Hz, 6 H, 2×CH$_3$). Anal. (C$_{31}$H$_{39}$Cl$_2$N$_5$O$_2$.) C,H,N,Cl.

Similar reaction of amine (XIII; R=H) and acid (X; R=Z =H) (see Example 2 for preparation) gave N-[3-(N-(2-chloroethyl) -N-ethylamino) phenyl]-N$^1$-[3-(N,N-dimethylaminomethyl) phenyl]-1,4-benzenedicarboxamide (5) (59%), mp 160°-161° C. (EtOAc/petroleum ether). $^1$H NMR 8.35 & 8.26 (2 ×s, 2 H, CONH, CONH ), 7.80 (s, 4 H, H -2',3',5',6'), 7.66 (d, J=8.2 Hz, 1 H, H-6''), 7.57 (s, 1 H, H-2''), 7.30 (t, J =7.7 Hz, 1 H, H-5''), 7.18 (t, J=8.4 Hz, 1 H, H-5), 7.11 (d, J=7.7 Hz, 1 H, H-4''), 6.89 (d, J=7.7 Hz, 1 H, H-4), 6.49 (dd, J=8.4, 2.3 Hz, 1 H, H-6), 3.61 (s, 4 H, NCH$_2$CH$_2$Cl), 3.41 (g, J=7.0 Hz, 2 H, NCH$_2$CH$_3$), 3.39 (s, 2 H, CH$_2$N(CH$_3$)$_2$), 2.24 (s, 6 H, N(CH$_3$)$_2$), 1.19 (t, J=7.0 Hz, 3 H, NCH$_2$CH$_3$). Anal.(C$_{27}$H$_{31}$ClN$_4$O$_2$) C, H, N, Cl.

Example 4

Synthesis of bis-N,N$^1$-[3-(N,N-dimethylaminomethyl) -phenyl]-1,4-benzenedicarboxamide (compound 6 of Table 1) by the method of Scheme 4.

Powdered 1,4-benzenedicarbonyl dichloride (XVIII; Z=H) (1.01 g, 5 mmol) was added to a stirred solution of 3-(N,N-dimethylaminomethyl) aniline (1.65 g, 11 mmol) in dry DMF (20 mL), and the reaction mixture was stirred at 25° C. for 30 min, and at 90° C. for 15 min. The cooled mixture was diluted with 1 N Na$_2$CO$_3$ to give bis-N,N$^1$-[3-(N,N-dimethylaminomethyl) phenyl]-1,4-benzenedicarboxamide (6). $^1$H NMR (free base in CDCl$_3$) [symmetric molecule]δ8.40 (s, 1 H, CONH), 7.79 (s, 2 H, H-2', 6'), 7.65 (d, J=8.0 Hz, 1 H, H-6), 7.57 (s, 1 H, H-2), 7.29 (m, 1 H, H-5), 7.11 (d, J=7.6 Hz, 1 H, H-4), 3.48 (s, 2 H, CH$_2$N(CH$_3$)$_2$), 2.23 (s, 6 H, N(CH$_3$)$_2$)-Dihydrochloride salt, mp>300° C. (MeOH/EtOAc). Anal.(C$_{26}$H$_{30}$N$_4$O$_2$.2HCl) C,H,N,Cl.

Example 5

Ability of compound 1 to alkylate DNA i) Preparation of labelled DNA fragment A 375 base pair EcoRI to BamHI fragment of pBR322 DNA was 3'-end labelled at the EcoRI site using Klenow fragment and $^{32}$P-dATP. The resulting labelled fragment was isolated on a 4% non-denaturing polyacrylamide gel. Given below is a partial sequence of the fragment from base pair 31 to 140:

```
         40         50         60         70         80
GCTTTAATGC GGTAGTTTAT CACAGTTAAA TTGCTAACGC AGTCAGGCAC

CGAAATTACG CCATCAAATA GTGTCAATTT AACGATTGCG TCAGTCCGTG
         90        100        110        120

130
CGTGTATGAA ATCTAACAAT GCGCTCATCG TCATCCTCGG
CACCGTCACC
GCACATACTT TAGATTGTTA CGCGAGTAGC AGTAGGAGCC
GTGGCAGTGG

140
CTGGATGCTG
GACCTACGAC
``` ii) Alkylation of labelled DNA

Labelled DNA (ca. 30,000 cpm) was incubated with the alkylating agent compound 1 in the presence of 1 μg of calf thymus DNA in 100 μl of 0.01 SHE buffer (pH=7.3, ionic strength=0.01) at 37° C. for 30 minutes. The drug to base pair ratio was adjusted to 0.20 against the carrier DNA. Although at this ratio more than one alkylation per labelled fragment occurred (Prakash et al., 1990), further experiments showed that at the lower ratio of 0.1, where less than one alkylation per fragment occurred, the alkylation pattern was nearly identical to that at 0.02 shown in FIG. 1. For experiments with Mg$^{2+}$, the reactions were carried out either in the presence of 30 mM NaCl or 10 mM MgCl$_2$ (final ionic strength=0.04). The reaction mixture was chilled in ice and modified DNA was precipitated with ethanol and lyophilised.

The modified DNA pellet was dissolved in 100 μl of 0.01 SHE (pH=7.3) and heated for 10 minutes at 90° C. Then 11 1 of 10 M piperidine was added to the solution and the reaction mixture was further heated for 10 minutes at 90° C. The sample was then lyophilised overnight, precipitated with ethanol and dissolved in 3 μls of sequencing dye made of 80% deionised formamide, 1% xylene cyanol and 1% bromophenol blue. The sample was denatured at 90° C. for two minutes prior to loading on a sequencing gel. The polyacrylamide gels were run as described previously (Prakash et al., 1990).

iii) DNA alkylation by compound 1

The strand cleavage pattern obtained by chemical treatment of the drug-treated DNA is shown in FIG. 1. Adenines in runs of As (33-35, 46-48) show strong bands, with weaker bands also seen for adenines in TA and AT sequences (57, 61, 85, 92 and 94). Very little guanine alkylation is observed, after taking into account the control and the loading variations. FIG. 2 shows the densitometer scans of the alkylation patterns obtained under different ionic strengths (panels middle and bottom) and in the presence of $MgCl_2$ (top panel). Changing the ionic strength from 0.01 to 0.04 does not affect the band distribution, but using the divalent cation $Mg^{2+}$ instead of the monovalent $Na^+$ leads to an increase in the intensities of bands at 57 and 61. Preliminary investigation using aniline mustards with varying drug/base pair ratios up to 0.10 showed that, on average, one alkylation or less per 375-bp labelled strand occurs (Prakash et al., 1990), implying that roughly one out of 20 molecules of drug available on average per strand eventually alkylates the DNA.

FIGS. 2 and 3 show that compound 1 preferentially alkylates adenines occurring in runs of As, and to a much smaller extent in 5'-AT and 5'-TA sequences. We have previously shown that $Mg^{2+}$ apparently inhibits adenine alkylation by DNA intercalator-targeted mustards in the major groove, but not in the minor groove (Prakash et al., 1990). The results summarized in FIG. 3 are thus consistent with compound 1 alkylating adenines at minor groove sites (presumably N3), since addition of $Mg^{2+}$ fails to diminish the band intensities, and in fact increases the degree of alkylation at adenines occurring in AT and TA sequences (eg bands 57 and 61). This may be due to the unusual conformation present in the ATZ and TA junctions, which may be further affected by the presence of $Mg^{2+}$ in the major groove. Crosslinking experiments show that compound 1 gives rise to about one interstrand crosslink from every 10 alkylation events; a much better ratio than those (ca. 1 in 20) which we have previously found with DNA intercalator-targeted aniline mustards (Prakash et al., 1990).

Example 6

Cross-linking and helix unwinding assays

These experiments were carried out as described previously (Prakash et al., 1990).

FIG. 3 shows the crosslinking of DNA by compound 1 at various concentrations. At a drug:bpr ratio of 0.04, on average one crosslink per 4362-bp DNA strand has occurred. This is based on a statistical model, in which the natural log ratio of the band intensities of the sample bands and that for the denatured DNA are used to determine the number of cross-links per fragment (Prakash et al., 1990). At the same input ratio there are not more than about 10 alkylation events per 4362-bp fragment [(4362bp/375bp)×(0.04 d per bp/0.10 d per bp) x (2 strands per fragment)=ca. 10], suggesting a crosslink to mono-adduct ratio of about 0.1. FIG. 4 shows the results from the helix unwinding assay. The drug does not completely remove the superhelical turns from supercoiled DNA even at a drug to basepair ratio of 0.40, indicating that the drug is not intercalated into DNA.

The negative results of the helix unwinding studies (FIG. 4) indicate that compound 1 does not intercalate into DNA. CPK models of compound 1 binding to DNA in the minor groove suggest that the molecule spans a distance of about 3 basepairs when the alkylating moieties are in closest proximity to the N3 sites of adenines on opposite strands. With such a binding mode, crosslinking would be most likely to take place in sequences AAT, ATT, TAA and TTA. Since we have shown here that alkylation is strongest in runs of As, the weak alkylation observed at AT junctions (eg at bases 57 and 61 which have runs of Ts preceding or following the A) may in fact be due to initial alkylation of adenines in the opposite strand followed by interstrand crosslinking.

Example 7

Biological activity of compound

Growth inhibition studies were performed as described in detail elsewhere (Wilson et al., 1989; Finlay et al., 1984). $IC_{50}$s were determined as the drug concentration needed to reduce the cell mass (protein content, measured after 72-78h by staining with methylene blue and measuring absorbance in a microplate photometer) to 50% of the mean value for 8 control cultures on the same 96-well plate. The ratio of $IC_{50}$ values against AA8 and UV4 cell lines is defined as $HF=IC_{50}(AA8)/IC_{50}(UV4)$.

Compound (1) had an $IC_{50}$ against P388 leukaemia cells of ca. 0.05 nM, and against AA8 cells of ca. 800 nM. It had an HF of 15, and showed significant activity against P388 leukaemia in vivo (ILS of 37% at an optimal dose of 9 mg/Kg, when given as a single intraperitoneal dose).

It is clear from these data that compound 1, a representative example of the compounds of general formula (I), is a potent cytotoxic agent, with in vivo anticancer activity. The present invention therefore also provides pharmaceutical compositions having antitumour activity and comprising at least one compound represented by the general formula (I), and one or more pharmaceutically-acceptable carriers or diluents.

References cited herein are listed on the following pages.

It will be clearly understood that the invention in its general aspects is not limited to the specific details referred to herein.

REFERENCES

BRAITHWAITE, A. W. & BAGULEY, B. C. Biochemistry, 1980 19, 1101

DENNY, W. A., ATWELL, G. J., BAGULEY, B. C. & CAIN, B. F. Journal of Medicinal Chemistry, 1979 22 134

FINLAY, G. J., BAGULEY, B. C. & WILSON, W. R. Anal. Biochem., 1984 139 272-277

GARCIA S. T., MCQUILLAN, A. & PANASCI, L. Biochem. Pharmacol., 1988 37 3189

HURLEY, L. H., LEE, C-S., MCGOVREN, J. P., WARPEHOSKI, M. A., MITCHELL, M. A. KELLY, R. C. & ARISTOFF, P. A. Biochemistry, 1988 27 3886

HURLEY, L. H. & NEEDHAM-VANDEVANTER, D. R. Accounts of Chemical Research, 1986 19 230

MITCHELL, M. A., JOHNSON, P. D., WILLIAMS, M. G. & ARISTOFF, P. A. Journal of the American Chemical Society, 1989 111 6428

PIEPER, R. O., FUTSCHER, B. W. & ERICKSON, L. C. Carcinogenesis, 1989 10 1307

PRAKASH, A. S., DENNY, W. A., GOURDIE, T. A., VALU, K. K., WOODGATE, P. D. & WAKELIN, L. P. G. Biochemistry, 1990 29 9799

TANG, M-S., LEE, C-S., DOISY, R., ROSS, L., NEEDHAMDEVANTER, D. R. & HURLEY, L. H. Biochemistry, 1988 27 893

WILSON, W. R., ANDERSON, R. F. & DENNY, W. A. J. Med. Chem., 1989 32 23

We claim:

1. A compound for use in treatment of a neoplastic disease state in a mammal, said compound having general formula (I)

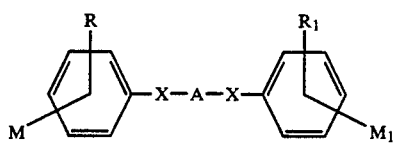

wherein M and $M_1$ separately represent H, aziridinyl, $N(Et)CH_2CH_2Y$ or $N(CH_2CH_2Y)_2$, where Y is Cl, Br, I or $OSO_2Me$: R and $R_1$ separately represent up to three of H or $CH_2Q$, such that at least one of R and $R_1$ is $CH_2NMe_2$, where Q is H, Me, $(CH_2)_nNMe_2$, $(CH_2)_mNHC(=NH)NH_2$ and n=0, 2–4 and m=2–4 with the proviso that n may only be 0 when R or $R_1$ is $—CH_2O$, and Q is $—(CH_2)_nNMe_2$; X represents CONH or NHCO; and A is

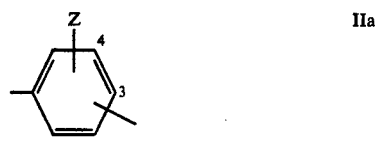

wherein Z=H, $CH_2Q$, $SO_2NHQ$ or CONHQ, where Q is H, Me, $(CH_2)_pNMe_2$, $(CH_2)_pNHc(=NH)NH_2$, and p=2 to 4, or an acid addition salt or N-oxide thereof.

2. A compound according to claim 1, selected from the group consisting of bis-N,N-40 -[3-(N-(2-chloroethyl)-N-ethylamino) -5-(N,N-dimethylaminomethyl)-phenyl]-1,4-benzenedicarboxamide, N-[3-(N-(2-chloroethyl)-N-ethylamino) -5-(N,N-dimethylaminomethyl)-phenyl]-N¹-[(3-(N,N-dimethyl-aminomethyl) phenyl]-1,4-benzenedicarboxamide, N-[3-(N-(2-chloroethyl) -N-ethylamino)-5-(N,N-dimethylaminomethyl) -phenyl]-N¹-phenyl-1,4-benzenedicarboxamide, N-[3-(N-(2-chloroethyl) -N-ethylamino)-5-(N,N-dimethylaminomethyl) phenyl]-N¹-[3-(N-(2-chloroethyl)-N-ethylamino)phenyl]-1,4-benzene-dicarboxamide, N-[3-(N-(2-chloroethyl) -N-ethylamino)phenyl]-N¹-[3-(N,N-dimethylaminomethyl) phenyl]-1,4-benzenedicarboxamide, and bis-N,N¹-[3-(N,,N-dimethylaminomethyl) phenyl]-1,4-benzenedicarboxamide.

3. A pharmaceutical composition for use in treatment of a neoplastic disease state in a mammal, said composition comprising a pharmaceutically-acceptable carrier and an effective amount of a compound of the general formula (I)

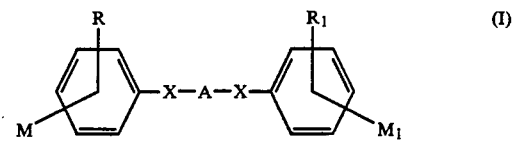

wherein M and $M_1$ separately represent H, aziridinyl, $N(Et)CH_2CH_2Y$ or $N(CH_2CH_2Y)_2$, where Y is Cl, Br, I or $OSO_2Me$; R and $R_1$ separately represent up to three of H or $CH_2Q$, such that at least one of R and $R_1$ is $CH_2NMe_2$, where Q is H, Me, $(CH_2)_nNMe_2$, $(CH_2)_mNHC(=NH)NH_2$ and n=0,2–4 and m=2–4 with the proviso that n may only be 0 when R or $R_1$ is $—CH_2Q$, and Q is $—(CH_2)_nNMe_2$; X represents CONH or NHCO; and A is

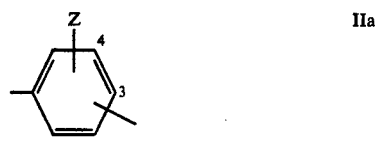

wherein Z=H, $CH_2Q$, $SO_2NHQ$ or CONHQ, where Q is H, Me, $(CH_2)_pNMe_2$, $(CH_2)_pNHc(=NH)NH_2$ and p=2 to 4, or an acid addition salt or N-oxide thereof.

4. The pharmaceutical composition of claim 3 wherein the compound is selected from the group consisting of bis-N,N'-[3-(N-(2-chloroethyl) -N-ethylamino)-5-(N,N-dimethylaminomethyl) phenyl]-1,4-benzenedicarboxamide, N-[3-(N-(2-chloroethyl) -N-ethyl-amino)-5-(N,N-dimethylaminomethyl) phenyl]-N¹-[(3-(N,N-dimethylaminomethyl)phenyl]-1,4-benzenedicarboxamide, N-[3-(N-(2-chloroethyl)-N-ethylamino)-5-(N,N-dimethylaminomethyl) -phenyl]-N¹-phenyl-1,4-benzenedicarboxamide, N-[3-(N-(2-chloroethyl)-N-ethylamino)-5-(N,N-dimethylaminomethyl) phenyl]-N¹-[3-(N-(2-chloroethyl) -N-ethylamino)phenyl]-1,4-benzenedicarboxamide, N-[3-(N-(2-chloroethyl)-N-ethylamino)phenyl]N¹-[3-(N,N-dimethylaminomethyl) phenyl]-1,4-benzenedicarboxamide, and bis-N,N¹-[3-(N,N-dimethylaminomethyl) phenyl]-1,4-benzenedicarboxamide.

5. A method for treatment of neoplastic disease state in a mammal, said method comprising administering to a mammal in need of such treatment a therapeutically effective amount of a compound of the general formula (I)

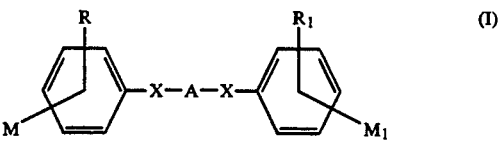

wherein M and $M_1$ separately represent H, aziridinyl, $N(Et)CH_2CH_2Y$ or $N(CH_2CH_2Y)_2$, where Y is Cl, Br, I or $OSO_2Me$; R and $R_1$ separately represent up to three of H or $CH_2Q$, such that at least one of R and $R_1$ is $CH_2NMe_2$, where Q is H, Me, $(CH_2)_nNMe_2$, $(CH_2)_mNHC(=NH)NH_2$ and n=0, 2–4 and m=2–4 with the proviso that n may only be 0 when R or $R_1$ is $—CH_2Q$, and Q is $—(CH_2)_nNMe_2$; X represents CONH or NHCO; and A is

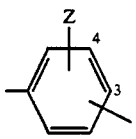

IIa wherein Z=H, CH$_2$Q, SO$_2$NHQ or CONHQ, where Q is H, Me, (CH$_2$)$_p$NMe$_2$, (CH$_{2p}$NHC(=NH)NH$_2$, and p=2 to 4, or an acid addition salt or N-oxide thereof.

6. The method of claim 5 wherein the compound is selected from the group consisting of bis-N,N'-[3-(N-(2-chloroethyl)-N-ethylamino)-5-(N,N-dimethylaminomethyl) phenyl]-1,4-benzenedicarboxamide, N-[3-(N-(2-chloroethyl)-N-ethylamino)-5-(N,N-dimethylaminomethyl)phenyl]-N$^1$-[(3-(N,N-dimethylaminomethyl) phenyl]-1,4-benzenedicarboxamide, N-[3-(N-(2-chloroethyl)-N-ethylamino)-5-(N,N-dimethylaminomethyl) phenyl]-N$^1$-phenyl-1,4-benzenedicarboxamide, N-[3-(N-(2-chloroethyl)-N-ethylamino)-5-(N,N-dimethylaminomethyl) phenyl]-N$^1$-[3-(N-(2-chloroethyl)-N-ethylamino)phenyl]-1,4-benzene-dicarboxamide, N-[3-(N-(2-chloroethyl)-N-ethylamino)phenyl]-N$^1$-[3-(N,N-dimethylaminomethyl) phenyl]-1,4-benzenedicarboxamide, and bis-N,N$^1$-[3-(N,N-dimethylaminomethyl)phenyl]-1,4-benzenedicarboxamide.

* * * * *

UNITED STATES PATENT AND TRADEMARK OFFICE
CERTIFICATE OF CORRECTION

PATENT NO. : 5,331,004
DATED : July 19, 1994
INVENTOR(S) : William A. Denny, et. al.

It is certified that error appears in the above-indentified patent and that said Letters Patent is hereby corrected as shown below:

Title page, item [73], Assignee: Add "Auckland Division Cancer Society of New Zealand, Inc., Auckland, New Zealand".

Signed and Sealed this

Fourteenth Day of February, 1995

Attest:

BRUCE LEHMAN

Attesting Officer

Commissioner of Patents and Trademarks